United States Patent [19]

Waitkus et al.

[11] 4,316,844

[45] Feb. 23, 1982

[54] POLYIMIDE DERIVATIVES HAVING UNSATURATED TERMINAL AMIC ACID GROUPS

[75] Inventors: Phillip A. Waitkus, Sheboygan, Wis.; Gaetano F. D'Alelio, South Bend, Ind.

[73] Assignee: Plastics Engineering Company, Sheboygan, Wis.

[21] Appl. No.: 115,482

[22] Filed: Jan. 25, 1980

[51] Int. Cl.$^3$ .................. C07D 403/10; C07D 403/12; C07D 403/14; C07D 519/00
[52] U.S. Cl. ........................... 260/326 S; 260/326 E; 260/326 C; 260/326 N; 526/259; 526/260; 526/263; 526/262; 528/26; 528/125; 528/170; 528/185; 528/188; 528/229; 528/321; 528/322; 528/352; 528/353; 542/437; 542/456; 546/68; 525/421; 525/426
[58] Field of Search ........... 260/326 S, 326 N, 326 E, 260/326 C; 528/125, 185, 177, 170, 188, 221, 229, 26, 321, 322, 352, 353; 526/260, 263, 259; 542/437, 456; 546/68

[56] References Cited

U.S. PATENT DOCUMENTS

| | | | |
|---|---|---|---|
| 3,897,395 | 7/1975 | D'Alelio | 260/326 C |
| 3,998,786 | 12/1976 | D'Alelio | 260/326 C |
| 4,168,360 | 9/1979 | D'Alelio | 528/188 |
| 4,168,366 | 9/1979 | D'Alelio | 528/188 |

*Primary Examiner*—Mark L. Berch
*Attorney, Agent, or Firm*—Walter J. Monacelli

[57] ABSTRACT

Novel compositions comprising unsaturated polyhemiamic acid compositions and processes for their preparation are disclosed herein. These new compositions are primarily derivatives of anhydride-terminated aromatic polyimides from which they are prepared by amidation to provide unsaturated amide groups having terminal —CH=CH$_2$ groups as hemi-amic acid groups or their derivatives. These new compositions are more tractable than the original anhydride-terminated polyimides and can be converted at appropriate lower temperatures to crosslinked, insoluble, infusible polymers without by-product formation thereby extending greatly the applications for which the aromatic polyimides can be employed. Also included are monomeric compounds containing unsaturated amide groups derived from monomeric tetracarboxylic dianhydrides. These are particularly useful as crosslinking agents.

19 Claims, No Drawings

POLYIMIDE DERIVATIVES HAVING UNSATURATED TERMINAL AMIC ACID GROUPS

BACKGROUND OF THE INVENTION

1. Field of the Invention

The invention relates primarily to new compositions comprising aromatic polyimides containing terminally unsaturated amide groups as part of hemi-amic acid or derivative groups. More specifically, it relates to such compositions in which the terminal amide groups are moieties that contain terminal $CH_2=CH-$ functions capable of polymerizing and forming crosslinked polymers. Still more specifically, it relates to such polyimide hemi-amic acid groups and to the crosslinked polymers obtained therefrom without the formation of by-products.

2. State of the Prior Art

Polyimides, as prepared from aromatic dianhydrides and aromatic diamines, are known to have the desired property of high heat resistance and high solvent resistance. Such polyimides, upon condensation to an infusible condition, generate by-products such as water and other vapors or gases which introduce voids into the fabricated products that detract from the expected good physical properties. In addition, because of these same desirable properties, they are untractable and therefore very difficult and expensive to work into desired shapes and forms.

Recent patents, such as U.S. Pat. Nos. 3,879,395 and 3,998,786, are directed to improving the tractability of the aromatic polyimides by attaching various terminal groups to polyimide oligomers whereby the chains are extended by coupling of the terminal groups. In both of these patents the coupling groups are attached as terminal imide moieties containing vinyl, propargyl, nitrile, etc. groups. Thus the terminal anhydride group is converted to an imide group containing a vinyl, nitrile, propargyl, etc. group. However in neither of these patents nor in any other related prior art reference has there been found any disclosure that the terminal anhydride group on each end could be converted to one amide moiety and a second amide or acid or ester moiety of which at least one or both could contain polymerizable structures. The amide groups present in the polyimide derivatives of this invention are tertiary amides devoid of hydrogen or the amide nitrogen. Therefore on heating, these amide groups do not convert to imide structures with accompanying by-product formation and simultaneous loss of crosslinking functionality. Consequently these structures contribute higher tractability to the composition and control of the number of crosslinking groups to values up to four with functionalities up to eight.

SUMMARY OF THE INVENTION

In accordance with the present invention, it has been found that tractable and curable polyimides may be prepared by converting each terminal anhydride group in an anhydride-terminated aromatic polyimide to an amide group containing at least one terminal $CH_2=CH-$ group as part of a hemi-amic acid or derivative group. Moreover it has also been found that these compositions have greater tractability than the corresponding anhydride-terminated and amine-terminated polyimides. Furthermore they can be fabricated and cured at practical temperatures and pressures to give insoluble, infusible products having improved heat and solvent resistance without by-product formation.

The unsaturated crosslinkable amides of this invention have the formula:

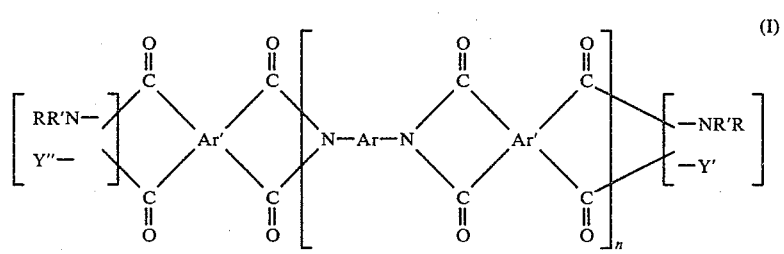

wherein:

Ar' is a tetravalent aromatic organic radical, the four carbonyl groups being attached directly to separate carbon atoms and each pair of carbonyl groups being attached to adjacent carbon atoms in the Ar' radical except that when the Ar' is a naphthalene radical one or both pairs of the carbonyl groups may be attached to peri carbon atoms;

Ar is a divalent aromatic organic radical;

n is zero or an integer of at least one, preferably 1–20;

R is an organic moiety having 1–20 carbon atoms including R';

R' is an organic moiety containing 2–14 carbon atoms and having a terminal $—CH_2=CH—$ structure;

Y'' is OH or X, and

X is halogen, preferably chlorine or bromine.

The amides (I) are conveniently prepared by amidation of the anhydride:

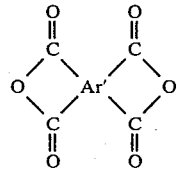

or the anhydride-terminated compound (II) of the formula:

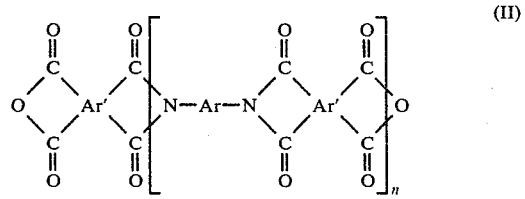

wherein Ar' is a tetravalent aromatic organic radical, preferably containing at least one ring of six carbon atoms, said ring being characterized by benzenoid unsaturation, the four carbonyl groups being attached directly to separate carbon atoms and each pair of carbonyl groups being attached to adjacent carbon atoms in the Ar' radical except that when Ar' represents the naphthalene radical one or both pairs of carbonyl groups may be attached to peri carbon atoms.

When the n in Formula II is zero, the formula becomes that of the dianhydride shown at the beginning of the paragraph. When n is one or more, Formula II contains two or more imide groups and represents polyimides used in this invention.

Amidation of (II) occurs in the terminal anhydride function first with the formation:

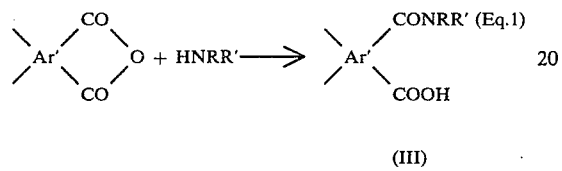

of a hemi-amic acid (III) which by continued amidation, yields the diamide (IV):

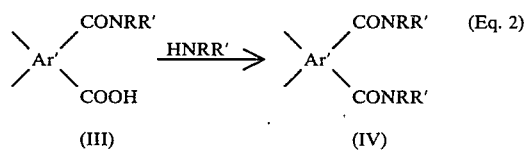

or by esterification yields the amide esters (V) which are useful per se or by interchange with HNRR' can be converted to amide structures (IV):

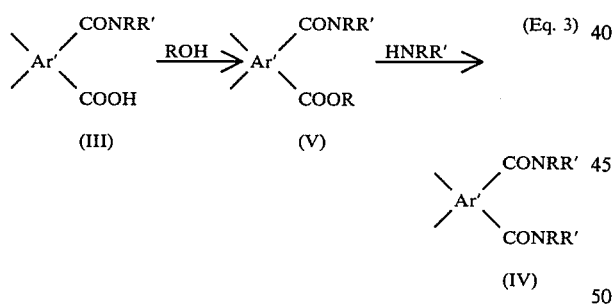

In some cases, such as when vinyl esters are desired in (V), transesterification may be used with vinyl esters such as vinyl acetate or vinyl benzoate to introduce a terminal vinyl structure, e.g.:

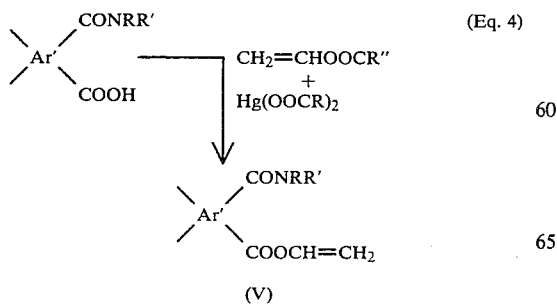

In the vinyl ester the R'' represents the hydrocarbon residue of an acid group such as ethyl in acetic acid, phenyl in benzoic acid, etc.

With regard to esterifications with alcohols that polymerize actively, particularly if heated, such as the vinyl benzyl alcohols, it is desirable to conduct all or part of the esterification by converting the anhydride or hemi-amic acid to the corresponding acid halide and performing the esterification at lower temperatures, e.g., at or below room temperature, thus:

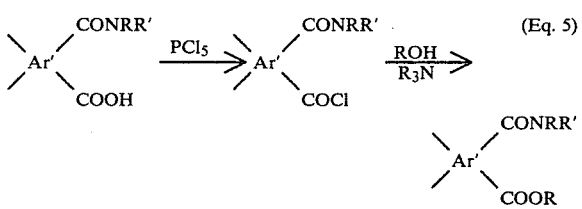

Alternatively, esterification can also be achieved by reacting a metal salt derivative of the terminal anhydride or hemi-amic acid group with an alkyl sulfate, e.g.:

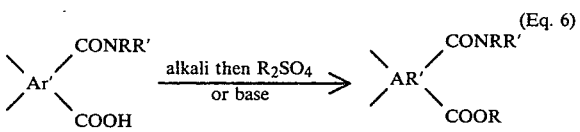

Alternatively, the anhydride function can be converted to the corresponding acid chloride (VII):

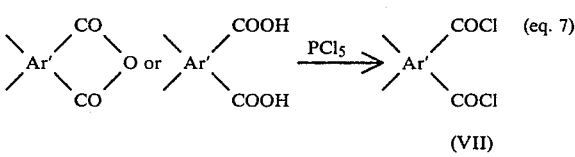

which is convertible to VI by reaction with HNRR' and by continued reaction with HNRR' to (IV) or with ROH to (V).

Also the amides of this invention may be prepared by amidating an amine-terminated compound of the formula VIII:

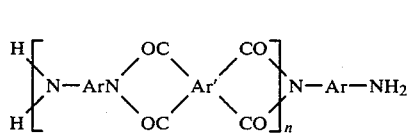

wherein Ar, Ar' and n has the same meaning as in Formula I with an unsymmetrical aromatic anhydride of the formula:

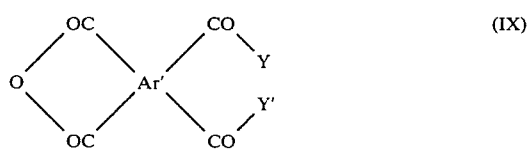

wherein Y represents NRR' and Y' represents NRR or OR. Thus:

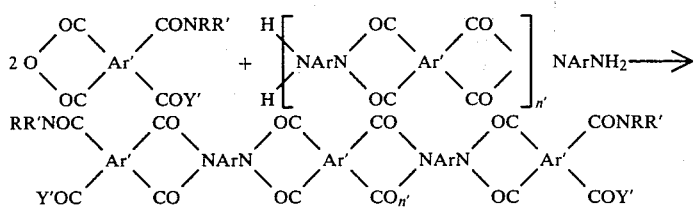

(Eq. 8)

The amine-terminated compounds (VIII) used hereinabove as intermediates in the preparation of the amides (I) of this invention as illustrated by Equation 8, are preferably oligomers prepared by reacting a molar excess, i.e., n+1 moles of an aromatic diamine, $H_2NArNH_2$, with n moles of an aromatic dianhydride

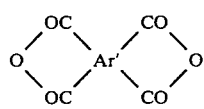

wherein Ar and Ar' have the same meaning as defined heretofore and the aromatic diamines and the aromatic dianhydrides are similar pairs of co-reactants used to prepare the anhydride-terminated compounds represented by Formula II. Polyimide amine-terminated oligomers of Formula VIII useful as intermediates may be conveniently prepared by the same process used to synthesize anhydride-terminated polyimides of Formula II except for the molar ratio of amine and anhydride used. Syntheses of the amine-terminated and anhydride terminated polyimide oligomers are exemplified in U.S. Pat. Nos. 3,897,395 and 4,058,505 and also hereinafter with specific reference, for example, to the synthesis of the anhydride-terminated polyimides.

Anhydride-terminated polyimides of Formula II used in the above reactions in the synthesis of polyimideamides of this invention are prepared by reacting a molar excess, i.e., n+1 moles of an aromatic dianhydride with n moles of an aromatic diamine. The aromatic dianhydride has the formula:

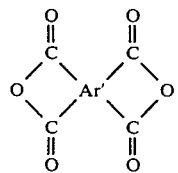

wherein Ar' is a tetravalent organic radical, preferably containing at least one ring of six carbon atoms, said ring characterized by benzenoid unsaturation, the four carbonyl groups being attached directly to separate carbon atoms and each pair of carbonyl groups being attached to adjacent carbon atoms in the Ar' radical except that when Ar' represents the naphthalene radical, one or both pairs of carbonyl groups may be attached to the peri carbon atoms.

The aromatic diamines useful in this preparation are represented by the formula $H_2N-Ar-NH_2$ wherein Ar is a divalent aromatic organic radical.

In preparing the anhydride-terminated polyimides, any of the aromatic tetracarboxylic acid dianhydrides known in the prior art can be used. Among the useful dianhydrides are 3,3',4,4'-benzophenonetetracarboxylic acid dianhydride, pyromellitic dianhydride, 2,3,6,7-naphthalene tetracarboxylic acid dianhydride, 1,4,5,6-tetracarboxylic dianhydride, 3,3',4,4'-diphenyl tetracarboxylic acid dianhydride, 1,2,5,6-naphthalene tetracarboxylic acid dianhydride, 2,2',3,3'-diphenyl tetracarboxylic acid dianhydride, 2,2-bis(3,4-dicarboxyphenyl)propane dianhydride, 3,4,9,10-perylene tetracarboxylic acid dianhydride, bis(3,4-dicarboxyphenyl)ether dianhydride, naphthalene-1,2,4,5-tetracarboxylic acid dianhydride, 2,2-bis(3,4-dicarboxyphenyl)propane dianhydride, 3,4,9,10-perylene tetracarboxylic acid dianhydride, bis(3,4-dicarboxyphenyl) ether dianhydride, naphthalene-1,2,4,5-tetracarboxylic acid dianhydride, naphthalene-1,4,5,8-tetracarboxylic acid dianhydride, decahydronaphthalene-1,4,5,8-tetracarboxylic acid dianhydride, 4,8-dimethyl-1,2,3,5,6,7-hexahydronaphthalene-1,2,5,6-tetracarboxylic acid dianhydride, 2,6-dichloronaphthalene-1,4,5,8-tetracarboxylic acid dianhydride, 2,7-dichloronaphthalene-1,4,5,8-tetracarboxylic acid dianhydride, 2,3,6,7-tetrachloronaphthalene-1,4,5,8-tetracarboxylic acid dianhydride, phenanthrene-1,8,9,10-tetracarboxylic acid dianhydride, cyclopentane-1,2,3,4-tetracarboxylic acid dianhydride, pyrrolidine-2,3,4,5-tetracarboxylic acid dianhydride, pyrazine-2,3,5,6-tetracarboxylic acid dianhydride, 2,2-bis(2,3-dicarboxyphenyl)propane dianhydride, 1,1-bis(2,3-dicarboxyphenyl)ethane dianhydride, 1,1-bis(3,4-dicarboxyphenyl)ethane dianhydride, bis(2,3-dicarboxyphenyl)methane dianhydride, bis(3,4-dicarboxyphenyl)methane dianhydride, bis(3,4-dicarboxyphenyl)sulfone dianhydride, and benzene-1,2,3,4-tetracarboxylic acid dianhydride. The first three mentioned dianhydrides are preferred.

Aromatic diamines useful in preparing the starting polyimides have the formula:

$$NH_2-Ar-NH_2$$

wherein Ar is a divalent aromatic organic radical. Preferred aromatic diamines are those wherein Ar is a divalent benzenoid radical selected from the group consisting of:

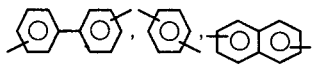

and multiples thereof connected to each other by $R^{III}$, e.g.,

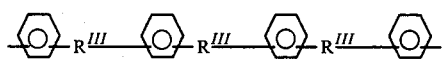

wherein $R^{III}$ is $-CH=CH-$;

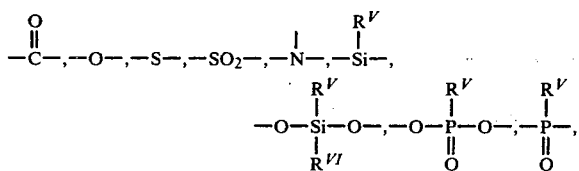

or an alkylene chain of 1-3 carbon atoms, wherein $R^V$ and $R^{VI}$ are each selected from the group consisting of alkyl and aryl containing one to six carbon atoms, e.g., methyl, ethyl, hexyl, n-butyl, i-butyl and phenyl. Preferred Ar' groups are:

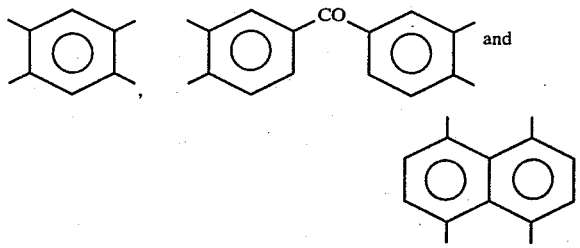

Examples of the aromatic diamines which are suitable for use in the present invention are 4,4'-diaminodiphenyl propane, 4,4'-diamino-diphenyl methane, benzidine, 3,3'-dichlorobenzidine, 4,4'-diamino-diphenyl sulfide, 3,3'-diamino-diphenyl sulfone, 4,4'-diamino-diphenyl sulfone, 4,4'-diamino-diphenyl-diphenylsilane, 4,4'-diamino-diphenyl ethyl phosphine oxide, 4,4'-diamino-diphenyl phenyl phosphine oxide, 4,4'-diamino-diphenyl N-methyl amine, 4,4'-diamino-diphenyl N-phenyl amine and mixtures thereof, 3,3'-dimethyl-4,4'-diaminodiphenylmethane, 3,3'-diethyl-4,4'-diaminodiphenylmethane, 3,3'-dimethoxy-4,4'-diaminodiphenylmethane, 3,3'-diethoxy-4,4-diaminodiphenylmethane, 3,3'-dichloro-4,4',4,4'-diaminodiphenylmethane, 3,3'-dibrome-4,4'-diaminodiphenylmethane, 3,3'-dicarboxy-4,4'-diaminophenylmethane, 3,3'-dihydroxy-4,4'-diaminophenylmethane, 3,3'-disulpho-4,4'-diaminodiphenylmethane, 3,3'-dimethyl-4,4'-diaminodiphenylether, 3,3'-diethyl-4,4'-diaminodiphenylether, 3,3'-dimethoxy-4,4,'-diaminodiphenylether, 3,3'-diethoxy-4,4'-diaminodiphenylether, 3,3'-dichloro-4,4'-diaminodiphenylether, 3,3'-dibromo-4,4'-diamino di-aminodiphenylether, 3,3'-dicarboxy-4,4'-diaminodiphenylether, 3,3'-dihydroxy-4,4'-diaminodiphenylether, 3,3'-disulfo-4,4'-diaminodiphenylether, 3,3'-dimethyl-4,4'-diaminodiphenylsulfide, 3,3'-diethyl-4,4'-diaminodiphenylsulfide, 3,3'-dimethoxy-4,4'-diaminodiphenylsulfide, 3,3'-diethoxy-4,4'-diaminodiphenylsulfide, 3,3'-dichloro-4,4'-diaminodiphenylsulfide, 3,3'-dibromo-4,4'-diaminodiphenylsulfide, 3,3'-dihyroxy-4,4'-diaminodiphenylsulfide, 3,3'-disulfo-4,4'-diaminodiphenylsulfide, 3,3'-dimethyl-4,4'-diaminodiphenylsulfone, 3,3'-diethoxy-4,4'-diaminodiphenylsulfone, 3,3'-dichloro-4,4'-diaminodiphenylsulfone, 3,3'-dicarboxy-4,4'-diaminodiphenylsulfone, 3,3'-disulfo-4,4'-diaminodiphenylsulfone, 3,3-diaminodiphenylsulfone, 3,3-diethyl-4,4'-diaminodiphenylpropane, 3,3,'-dimethoxy-4,4'-diaminodiphenylpropane, 3,3'-dibromo-4,4'-diaminodiphenylpropane, 3,3'-dichloro-4,4'-diaminodiphenylpropane, 3,3'-dicarboxy-4,4'-diaminodiphenylpropane, 3,3-dihydroxy-4,4'-diaminodiphenylpropane, 3,3'-disulfo-4,4'-diaminodiphenylpropane, 3,3'-dimeth-yl-4,4'-diaminobenzophenone, 3,3-dimethoxy-4,4'-diaminobenzophenone, 3,3'-dichloro-4,4'-diaminobenzophenone, 3,3'-dibromo-4,4'-diaminobenzophenone, 3,3'-dicarboxy-4,4'-diaminobenzophenone, 3,3'-dihydroxy-4,4'-diaminobenzophenone, 3,3'-disulphodiaminobenzophenone, 3,3'-diaminodiphenylmethane, 3,3'-diaminodiphenylether, 3,3'-diaminodiphenylsulfide, 3,3-diaminodiphenylsulfone, 3,3-diaminodiphenylpropane, 3,3'-diaminobenzophenone, 2,4-diaminotoluene, 2,5-diaminotoluene, 1-isopropyl-2, 4-phenylenediamine, 2,4-diaminoanisole, 2,4-diaminomonochlorobenzene, 2,4-diaminofluorobenzene, 2,4-diaminofluorobenzene, 2,4-diaminobenzoic acid, 2,4-diaminophenol and 2,4-diaminobenzenesulfonic acid and phenylene diamines. Preferred diamines are 4,4'-oxydianiline, 4,4'-sulfonyldianiline, 4,4'-methylene dianiline, 4,4'-diaminobenzophenone, 4,4'-diaminostilbene and the phenylene diamines, 2,4-diaminotoluene and all the meta and para isomers of $N_2NC_6H_4OC_6H_4OC_6H_4NH_2$.

The monoamines used in introducing the $CH_2=CH-$ containing tertiary amide groups (devoid of hydrogen atoms on the nitrogen atoms) into the polyimides of this invention are secondary amines and are represented by the formula HNRR'. The hydrogen attached to the secondary amine is eliminated in the reaction that forms the amide.

In HNRR', R' and R have the same meaning as defined for Formula (I). A few typical examples of such amines are:

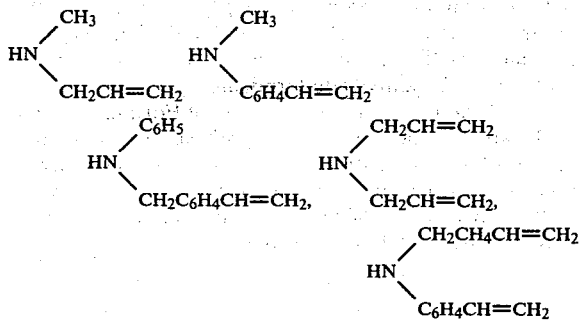

A few illustrative examples of R', that is, an organic moiety containing 2 to 14 carbon atoms and a terminal $-CH=CH_2$ group are:

$CH_2=CH-$, $CH_2=CH-CH_2-$, $CH_2=CHCH(CH_3)-$, $CH_2=CHC_6H_4-$, $CH_2=CHC_6H_4CH_2-$, $CH_2=CHCH_2CH_2C_6H_4-$, $CH_2=CHCH_2C_6H_4-$, $CH_2=CHCH_2C_6H_4CH_2-$, $CH_2=CHC_6H_4OC_6H_4-$, $CH_2=CHC_6H_4SO_2C_6H_4-$, $CH_2=CHC_6H_4OCH_2CH_2CH_2CH_2-$, $CH_2=CHC_6H_4OCH_2CH_2CH_2CH_2CH_2-$, $CH_2=CHOCH_2CH_2-$, $CH_2=CHOCH_2CH_2CH_2-$, $CH_2=CHOC_6H_4-$, $CH_2=CHCH_2OC_6H_4-$, $CH_2=CHOC_6H_4OCH_2CH_2-$, $CH_2=CHOC_6-H_4OCH_2(CH_2)_4CH_2-$, $CH_2=CHOOCC_6H_4-$, etc. For reasons of economy and commercial availability of intermediates for synthesis, the preferred R' groups are $CH_2=CH-$, $CH_2=CHC_6H_4-$, $CH_2=CHC_6H_6-$ and $CH_2=CHC_6H_4CH_2-$.

The corresponding hydroxy compounds have the formula R'OH and are classified as alcohols or phenols and are used to introduce ester groups into the compositions of this invention as shown hereinabove. In the case of the vinyl groups the $CH_2=CH-$ group is introduced as indicated above by means of the esters of vinyl alcohol, namely the vinyl esters $CH_2=CHOCOR'$ wherein R' is any hydrocarbon moiety containing 1 to 20 carbon atoms, preferably 2 to 6 carbon atoms as represented by vinyl acetate, vinyl benzoate, vinyl butyrate, etc.

Illustrative examples of R are, in addition to R', the organic moieties containing 1 to 20 carbon atoms, e.g.: $-CH_3$, $-CH_2CH_3$, $-CH_2CH_2CH_3$, $HC(CH_3)_2$, $-CH_2CH_2CH_2CH_2$,

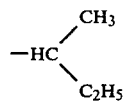

$-CH(CH_3)CH(CH_3)_2$, $-(CH_2)_4CH_3$, $-CH_2CH(C_2H_5)_2$, $-CH_2CH=CHCH_3$, $-(CH_2)_{11}CH_3$, $-(CH_2)_{19}-CH_3$, $-C_6H_5$, $-C_6H_{11}$, $-C_6H_4CH_3$, $-C_6H_4C_6H_5$, $-C_{10}H_7$, $-CH_2C-H_2OC_6H_5$, $-CH_2C_6H_4SO_2C_6H_5$, $-CH_2C-H_2OOCC_6H_5$, $-CH_2C_6H_5$, $-CH_2C_6H_{11}$, $-CH_2C_{10}H_7$, etc. The corresponding hydroxy compounds have the formula ROH.

Monoamines which may be used to introduce a second amide group into the polyimides of this invention without introducing another vinyl group have the formula HNRR in which neither R is R'. However R can contain $CH=C-$ or $-C\equiv C-$ moieties, some examples of which are: $CH\equiv CCH_2-$, $CH\equiv C-CH(CH_3)-$, $CH\equiv CCH_2CH_2-$, $CH\equiv CC_6H_4$, $CH\equiv CC_6H_4CH_2-$, $CH\equiv CCH_2CH_2C_6H_4-$, $CH\equiv CCH_2C_6H_4CH_2-$, $CH\equiv CC_6H_4OC_6H_4-$, $CH\equiv CC_6H_4SO_2C_6H_4$, $CH\equiv CC_6H_4OCH_2CH_2CH_2C-H_2-$, $CH\equiv CC_6H_4OCH_2CH_2CH(CH_3)CH_2-$, $CH\equiv CCH_2OCH_2CH_2-$, $CH\equiv CCH_2OCH_2CH_2C-H_2-$, $CH\equiv CCH_2OC_6H_4-$, $CH\equiv CCH_2CH_2OC_6-H_4-$, $CH\equiv CCH_2CH(CH_3)C_6H_4OCH_2CH_2-$, $CH\equiv CCH_2OC_6H_4OCH_2(CH_2)_3CH_2-$, $CH\equiv CCH_2OOCC_6H_4-$, $CH\equiv CCH_2OOCCH_3$, etc.

The polyimide starting materials used in the process of this invention may be prepared conveniently as shown in U.S. Pat. Nos. 3,897,395 and 4,058,505 by reacting the dianhydride with the diamine in a phenol solvent of the formula:

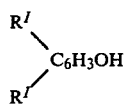

where each $R^I$ is hydrogen or a methyl radical in the presence of certain organic azeotroping agents, particularly cyclic hydrocarbons of 6 to 8 carbon atoms and most preferably benzene or toluene until most of the water of reaction is eliminated. The reaction temperature is less than 140° C. and also should be below the boiling point of the phenol used but higher than the boiling point of the azeotroping agent. The vapor phase temperature lies between that of the water azeotrope and no higher than 95° C. As the water of reaction and azeotroping agent are removed from the reaction mixture, quantities of the azeotroping agent are returned to the reaction mixture so as to maintain the temperature and reaction mixture volume substantially constant. It is preferred that the process be continuous with continuous removal of water and continuous return of azeotroping agent. This is conveniently done by the use of a conventional Dean-Stark trap and condenser wherein after the azeotrope condenses, the water preferably sinks to the bottom of the trap for subsequent removal and the azeotroping agent overflows the trap and returns to the reaction mixture. Initially the trap is filled with azeotroping agent. For brevity, this apparatus will be referred to herein as cresol-benzene azeotropic apparatus.

By using an excess of the anhydride, the terminal groups of the polyimide will be anhydride groups. The more excess there is of the anhydride, the shorter will be the molecular length. Advantageously the amount of excess anhydride is calculated in accordance with the desired length or molecular weight of the desired starting polyimide.

The products of this invention can be converted to the insoluble, infusible state by heat alone, such as by heating at temperatures in the range of 200° C. to 350° C., or even at lower temperatures, such as 100° C. to 200° C., or, if desired, by the addition of catalysts that generate free radicals, such as benzoylperoxide, the perbenzoates, cumyl mono and diperoxides, and a host of others that are well known in the vinyl monomer art, which include redox systems which promote polymerization of $CH_2=CH-$ containing monomers at or even below room temperature, or by ionizing radiation or ultraviolet radiation, etc.

These products can be compounded with fillers of all sorts in the preparation of molding compounds, such as with graphite and quartz fibers or fillers to maintain high temperature resistance, etc.

The hemi-amic acids and derivatives of this invention are particularly useful as coatings and bonding agents for metals such as iron, copper, aluminum, steel, etc. either alone or as mixtures with the tetraamides containing two to four terminal $CH_2=CH-$ structures. Also important is the fact that these new polyamides copolymerize with polyimides not containing terminal amide groups but imide structures which have terminal $CH_2=CH-$, $CH\equiv C-$ or

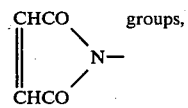

a number of which are disclosed in U.S. Pat. No. 3,998,786.

The new polyimide amides of this invention can be used as varnishes and coatings in appropriate solvents which depend on the nature of the constituent diamine and dianhydrides used in the synthesis of the polyimide amides.

In most cases the solvent is an aprotic organic compound having a dielectric constant between 35 and 40, preferably one which is water soluble. Representative aprotic compounds are: N,N-dimethylformamide, N,N-diethylformamide, N,N-dimethylmethoxyacetamide, N-methyl caprolactam, caprolactam, N,N-dimethylacetamide, N,N-diethylacetamide, dimethyl sulfoxide, N-methyl-α-pryyolidone, tetramethylurea, hexamethylphosphonamide, tetramethylene sulfone, N,N,N',N'-tetramethylethylmalonamide, N,N,N',N'-tetramethyl glutaramide, N,N,N',N'-tetramethylsuccinamide, thiobis(N-dimethylacetamide), bis(N,N-dimethylcarbamylmethyl)ether, N,N,N'N'-tetramethylfuraramide, methylsuccinonitrile, N,N-dimethyl-cyanoacetamide, N,N-dimethyl-β-cyano-propionamide, N-formyl-piperdine and butyrolactone, etc.

Of the solvents, dimethylacetamide is most preferred. Other preferred solvents are dimethylformamide, N-methyl pyrrolidone, dimethyl sulfoxide, butyrolactone and caprolactum.

In many cases, non-aprotic solvents can be used. For example, xylene, phenol, anisole, benzonitrile, acetophenone, methylphenylether, methylene chloride, chloroform, carbon tetrachloride or mixtures of these with each other, the aprotic solvents or with relatively poor solvents such as benzene, toluene, cyclohexane, cyclohexene, dioxane, butyl cellosolve and the like.

In the practice of this invention the specific nature of Y and Y" in Formula I is very important in avoiding the formation of by-products which are retained and detrimental when the compositions of Formula I are subjected to thermal treatment either to achieve curing and crosslinking of this composition, or after curing, when the composition is subjected to the long term stress of high temperatures in a particular application of the formed, cured fabricated parts such as in moldings, laminated products, fiber-reinforced shapes, wire and other filament coated products, etc. For example, if a primary amine H$_2$NR' is used instead of HNRR' in Eq. 1 in the formation of hemi-amic acid, this hemi-amic acid, when heated, will imidize with the elimination of H$_2$O as illustrated below:

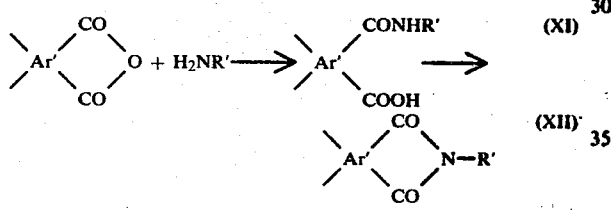

This imidization will occur even if the —COOH function is changed to —COOR, —COOR', —CONHR, —CONHR', —CONRR', CONRR, —CONRR', —COX as long as there remains an active amide hydrogen in the —CONHR' moiety, thus:

| Ar | CONHR' $\xrightarrow{\Delta}$ | | (XII) + ROH |
|---|---|---|---|
| " | (COOR) | " | (XII) + R'OH |
| " | (COOR') | " | (XII) + H$_2$NR' |
| " | (CONHR') | " | (XII) + H$_2$NR' + H$_2$NR |
| " | (CONHR) | " | (XII) + H$_2$NR' |
| " | (CONHR') | " | (XII) + HNRR' |
| " | (CONRR') | " | (XII) + HNRR |
| " | (CONRR) | " | (XII) + HNRR' |
| " | (CONRR') | " | (XII) + HX |
| " | (COX) | " | |

In contrast, when Y and Y' are as defined in the practice of this invention, imidization does not occur:

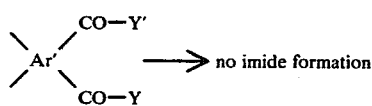

and the Y' moieties function to produce crosslinkages without the formation of by-products.

A particular advantage accrues to the practice of this invention. It is obvious that in polyimides that depend for crosslinking on terminal imide functional groups, as for example:

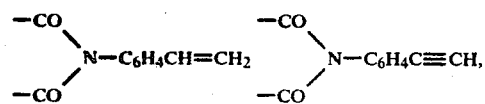

etc., there are only two polymerizable crosslinking groups per polymer chain, and as the chain length increases as it does with an increase in the value of n as in (I), the crosslink density, i.e., the number of crosslinks per n number of segmers, decreases and the heat distortion value of the composition under load decreases. It is desirable therefore, to be able to increase the crosslink density of such composition. This is now achieved by converting the terminal anhydride groups to Y and Y' which cannot imidize. The products have chains with only one crosslinking function at each end of the chain. By the practice of this invention, it is possible, if desired, to adjust the crosslink density as a function of only one crosslinking moiety at the end of each chain to as high as four at each end, or a total of eight for each chain, as shown in such structures as:

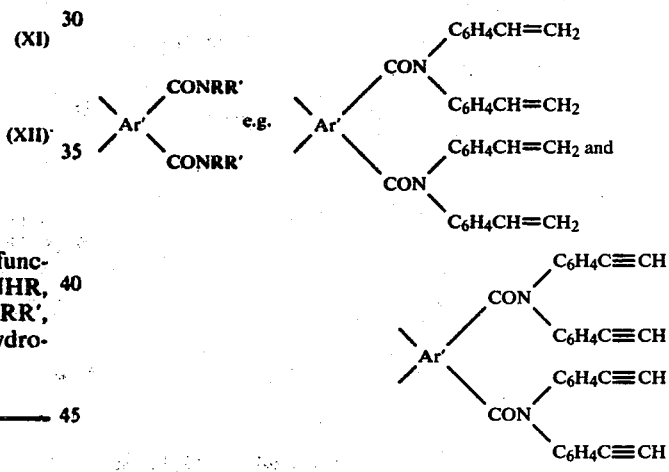

In addition, the increased number of such functional groups contribute to an increase in the rate of curing which has industrial economic importance.

The composition of this invention finds utility in the broad field of polyimide technology as in molding compounds, laminated products as impregnants for porous bodies, varnishes for a wide variety of substances including sheets, filaments, etc. of metals, glass, carbons, encapsulating compounds, etc.

SPECIFIC EMBODIMENTS OF THE INVENTION

The invention is illustrated by the following examples which are intended merely for purpose of illustration and are not to be regarded as limiting the scope of the invention or the manner in which it may be practiced. Unless specifically indicated otherwise, parts and percentages are given by weight.

EXAMPLE I

Preparation of Anhydride-Terminated Oligomeric Polyimide #1

Into a 100 ml three-neck, round bottom flask equipped with a magnetic stirrer, thermometer, condenser, gas inlet tube, dropping funnel, etc. there is placed under nitrogen atmosphere a solution of benzophenone-tetracarboxylic acid anhydride (BTCA) (6.44 g, 0.02 mole) in 25 ml of dimethylacetamide (DMAC). Then a solution of 4,4'-oxydianiline (ODA) (2.00 g, 0.01 mole) in 15 ml of DMAC is added over a period of 15 minutes. The reaction, which is exothermic, is maintained at 40° C. during the addition following which it is heated at 85° C.–90° C. for 15 minutes. To this clear amber-coated solution, acetic anhydride (3.06 g, 0.03 mole) is added and the mixture is heated to 125° C. Within 15 minutes, a yellow precipitate is formed. After heating the reaction mixture for one hour the solvents are removed in a rotary flash evaporator. The residual light yellow solid is washed with anhydrous ether and dried in a vacuum oven at 140° C. to afford a quantitative yield. It softens slightly on a Fisher-Johns melting point apparatus at 120° C. and does not melt when heated to 300° C. The product is soluble in m-cresol and N-methyl-2-pyrrolidone and only slightly soluble in boiling benzonitrile, acetophenone or DMAC. The elemental analysis is found to be for C: 68.3% and for H: 2.4%, which are in good agreement with the calculated values for $C_{46}H_{20}N_2O_{13}$ having the formula:

$O(OC)_2C_6H_3COC_6H_3(CO)_2NC_6H_4OC_6H_4$-$N(OC)_2C_6H_3COC_6H_3(CO)_2O$

EXAMPLE II

Hemi-Amic Acid of Polyimide of Example I

Into the reaction equipment used in Example I there is placed 25 ml of m-cresol, 4.04 gm of polyimide #1, 0.80 gm of N,N-methylallylamine and the mixture is heated at reflux for one hour. Water:methanol (50:50) is added to the precipitate and washes the polymer product which is isolated by filtration and dried in a vacuum oven at 130°–140° C. to give an almost quantitative yield of 4.38 grams. The elemental analysis of 68.1% carbon and 3.93% hydrogen are in good agreement with the calculated values for $C_{54}H_{38}N_4O_{13}$ having the formula:

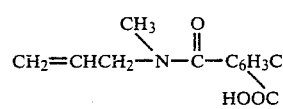

EXAMPLE III

Preparation of Anhydride-Terminated Polyimide #2

Using the m-cresol-benzene azeotropic procedure, there is allowed to react benzophenone-tetracarboxylic acid anhydride (BTCA) (4.0279 g, 0.0125 mole) and 1,3-di(3-aminophenoxy)benzene (DAPB-3,3) (2.9233 g, 0.01 mole) in 40 ml of m-cresol and 10 ml of benzene. There is obtained 5.76 gm of polyimide #2 which is a light yellow powder, soluble in m-cresol, DMAC, sulfolane and dioxane. In a Fisher-Johns melting point apparatus, this melts at 200° C. The TGA in air shows losses at 200° C. of 1%, 3% at 300° C., 4% at 400° C., 5% at 500° C. and 17% at 600° C. The elemental analysis is: C: 71.4% and H: 3.2% which are in excellent agreement with the calculated values for $C_{157}H_{78}O_{35}N_8$ of the formula:

$O(OC)_2C_6H_3COC_6H_3(CO)_2[NC_6H_4OC_6H_4OC_6H_4$-$N(OC)_2C_6H_3COC_6H_3(CO)_2]_4O$

EXAMPLE IV

Preparation of Hemi-amic Acid of Anhydride-Terminated Polymer #2

Part A

In the same equipment used in Example I, there is added 5.28 g of polyimide #2, 40 ml of m-cresol and 0.30 gm of N,N-methyl-allyl amine and the mixture heated to 100° C. for one hour. A liquid sample is then withdrawn and analyzed. The elemental analysis is found to show C: 71.00%, N: 4.97% and H: 3.67%, which values are in good agreement with the calculated values for $C_{165}H_{96}O_{35}N_{10}$ having the hemi-amic formula:

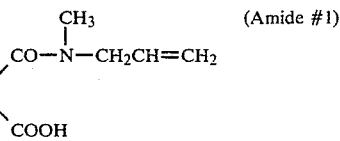

Part B—Ester Derivative of Amide #2

The apparatus is converted by the addition of a Dean-Stark trap to a continuous azeotroping apparatus. The trap is filled with toluene, 10 ml of benzene is added to the reaction mixture together with 5 ml of allyl alcohol, and the reaction mixture is heated at reflux for 5 hours or until no more water of reaction is formed. Two grams of sodium bicarbonate is added to the mixture to neutralize the toluene sulfonic acid. The solution is then filtered and concentrated on a rotary evaporator and vacuum dried to constant weight at 130°–135° C. The isolated product is washed with ether and redried in a vacuum oven. The elemental analysis is found to give C: 71.59% and H: 3.81%, which values are in good agreement with the calculated values for the diamide-diester $C_{171}H_{104}O_{35}N_{10}$ having the formula:

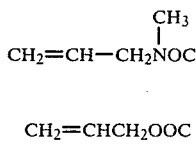

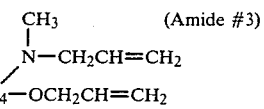

$C_6H_3COC_6H_3(CO)_2[NC_6H_4OC_6H_4OC_6H_4N(OC)_2-C_6H_3COC_6H_3(CO)_2]_4-OCH_2CH=CH_2$

On a Fisher-Johns melting point apparatus, the diamide-diester melts at 190°–195° C., thickens above 210° C. and crosslinks and cures at 210°–250° C.

EXAMPLE V

Preparation of Hemi-Amic Acid Chloride

Part A of Example IV is repeated to obtain the hemi-amic which is isolated by evaporation of solvent from the reaction mixture and the residue is washed with ether and dried. Then to a reaction flask is added 53.5 gms of this hemi-amic, 250 ml of dioxane, an excess (10 grams) of thionylchloride, and the mixture is refluxed until no more $SO_2$ or HCl is liberated. The mixture is evaporated to dryness in a rotary evaporator at 15 mm pressure to afford an almost quantitative yield (54 g) of a product whose analysis shows 2.24% chlorine, which value is in good agreement with the calculated value for the hemi-amic acid chloride:

EXAMPLE VI

Conversion of the Hemi-Amic Acid Chloride to an Amide-Ester

In a suitable reaction flask, 20 ml of dioxane is added together with 5.6 g of the acid chloride of Example V, 10 g of anhydrous methanol (an excess) and 0.41 g of triethylamine in 5 ml of dioxane as a hydrohalide acceptor. The mixture is heated at reflux for 3 hours then precipitated with water, filtered, washed with methanol and dried to yield the diamide-diester:

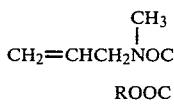

$ROOC-C_6H_3COC_6H_3(CO)_2=[NC_6H_4OC_6H_4N(OC)_2C_6H_3COC_6H_3(CO)_2]_4-NCH_2CH=CH_2$

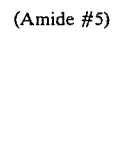

in which R is $CH_3$. When heated at 230° C. the amide-ester yields crosslinked polymers. Replacement of the methanol by other esterfiable ROH compounds yields the corresponding esters as shown in Table I. Isolation can also be achieved by precipitation with organic liquid in those cases where the ROH compound is not water soluble.

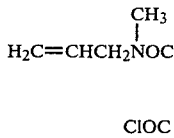

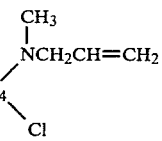

$C_6H_3COC_6H_3(CO)_2=[NC_6H_4OC_6H_4OC_6H_4N(OC)_2C_6H_3COC_6H_3(CO)_2]_4$

TABLE I

| Amide # | ROH Used | R in Ester |
|---|---|---|
| 6 | $C_2H_5OH$ | $C_2H_5-$ |
| 7 | $C_4H_9OH$ | $C_4H_9-$ |
| 8 | $C_{12}H_{25}OH$ | $C_{12}H_{25}-$ |
| 9 | $CH_2=CHC_6H_4CH_2OH$ | $CH_2=CHC_6H_4CH_2-$ |
| 10 | $CH_2=CHC_6H_4OH$ | $CH_2=CHC_6H_4-$ |
| 11 | $CH_2=C-CH_2OH$ <br> $\|$ <br> $Cl$ | $CH_2=C-CH_2-$ <br> $\|$ <br> $Cl$ |
| 12 | $C_6H_{11}OH$ | $C_6H_{11}-$ |
| 13 | $C_6H_5CH=CHCH_2OH$ | $C_6H_5CH=CHCH_2-$ |
| 14 | $CH_2=CHOCH_2CH_2CH_2OH$ | $CH_2=CHOCH_2CH_2CH_2-$ |
| 15 | $CH_2=CHOC_6H_4OC_6H_4OC_6H_4OH$ | $CH_2=CHOC_6H_4OC_6H_4OC_6H_4-$ |
| 16 | $CH_2=CHOOCC_6H_4OH$ | $CH_2=CHOOCC_6H_4-$ |
| 17 | $CH_2=CHCOOCH_2CH_2OH$ | $CH_2=CHCOOCH_2CH_2-$ |
| 18 | $CH_2=CHOC_6H_4OCH_2CH_2OH$ | $CH_2=CHOC_6H_4OCH_2CH_2-$ |
| 19 | $C_6H_2Cl_3OH$ | $C_6H_2Cl_3-$ |
| 20 | $CH\equiv C-CH_2OH$ | $CH\equiv C-CH_2-$ |
| 21 | $CH\equiv C-C_6H_4OH$ | $CH\equiv C-C_6H_4-$ |
| 22 | $CH\equiv C-CH_2C_6H_4OH$ | $CH\equiv C-CH_2C_6H_4-$ |
| 23 | $CH\equiv C-C_6H_4CH_2OH$ | $CH\equiv C-C_6H_4CH_2-$ |

Instead of thionyl chloride, the phosphorous halides such as $PCl_3$, $PCl_5$, etc. can be used in the conversion of the acid to the acid chloride.

Amides #6 through 23 crosslink when heated in the range of 200° to 350° C.; particularly suitable for preparing more highly crosslinked polymers are amides #10, #16, #17, #20 and #21.

EXAMPLE VII

Conversion of the Hemi-Amic Acid Chloride To a Terminal Diamide

In a suitable reaction flask containing 20 ml of dry dioxane and using the procedure of Example VI, there is added together 5.4 g of the acid chloride of Example V, an equivalent amount of triethylamine ($\simeq$0.41 g) dissolved in 5 ml of dioxane as a hydrohalide acceptor and then an equivalent amount of the secondary amine. The mixture is reacted and the product isolated as described in Example VI. Table II lists the amines reacted in individual reactions and the structure of the resulting amide group derived from the acid chloride function, such group being located terminally at the end of the chains, as given in the following equation:

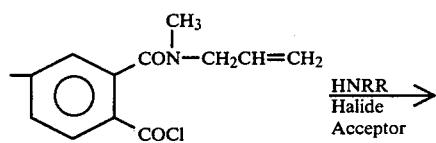

TABLE II

| A-mide # | Amine Used (HNRR) | New Amine Group (—CONRR) |
|---|---|---|
| 24 | HN(CH₃)(CH₃) | —CON(CH₃)(CH₃) |
| 25 | HN(C₁₈H₃₇)(C₁₈H₃₇) | —CON(C₁₈H₃₇)(C₁₈H₃₇) |
| 26 | HN(CH₂CH=CH₂)(CH₂CH=CH₂) | —CON(CH₂CH=CH₂)(CH₂CH=CH₂) |
| 27 | HN(CH₂C₆H₄CH=CH₂)(CH₂C₆H₄CH=CH₂) | —CON(CH₂C₆H₄CH=CH₂)(CH₂C₆H₄CH=CH₂) |
| 28 | HN(CH₂C₆H₄CH=CH₂)(C₆H₄CH=CH₂) | —CON(CH₂C₆H₄CH=CH₂)(C₆H₄CH=CH₂) |
| 29 | HN(CH₂C≡CH)(CH₂C≡CH) | —CON(CH₂C≡CH)(CH₂C≡CH) |
| 30 | HN(CH₂C₆H₄C≡CH)(CH₃) | —CON(CH₂C₆H₄C≡CH)(CH₃) |
| 31 | HN(CH₂C₆H₄C≡CH)(CH₂C₆H₄C≡CH) | —CON(CH₂C₆H₄C≡CH)(CH₂C₆H₄C≡CH) |

Amides #24 to #31, inclusive, crosslink when heated in the range of 225° to 360° C.

EXAMPLE VIII

The procedure of Example IVA is repeated using diallylamine, HN(CH₂CH=CH₂)₂ instead of N,N-methylallylamine. The resultant hemi-amic acid is then converted to the acid chloride by the procedure of Example V to yield:

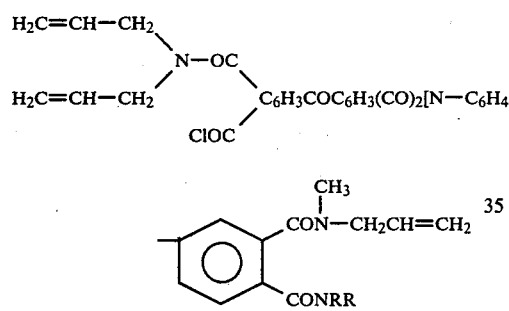

(Amide #32)

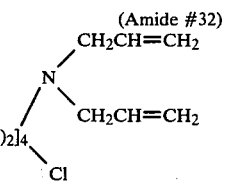

Reaction with the amines listed in Table II converts the acid chloride function to the corresponding type of amide groups listed in Table II, thus:

| Amide # | New Amide Group (—CONRR) |
|---|---|
| 33 | —CON(CH₃)(CH₃) |
| 34 | —CON(C₁₈H₃₇)(C₁₈H₃₇) |
| 35 | —CON(CH₂CH=CH₂)(CH₂CH=CH₂) |

-continued

| | |
|---|---|
| 36 | —CON⟨CH₂C₆H₄CH=CH₂ / CH₂C₆H₄CH=CH₂ |
| 37 | —CON⟨CH₂C₆H₄CH=CH₂ / C₆H₄CH=CH₂ |
| 38 | —CON⟨CH₂C≡CH / CH₂C≡CH |
| 39 | —CON⟨CH₂C₆H₄C≡CH / CH₃ |
| 40 | —CON⟨CH₂C₆H₄C≡CH / CH₂C₆H₄C≡CH |
| 41 | —CON⟨CH₃ / CH₂CH=CH₂ |
| 42 | —CON⟨CH₃ / CH₂C≡CH |

It is to be noted that amide numbers 35, 36, 37, 38 and 40 have four polymerizable groups in each end-group on each chain end for a total of eight polymerizable groups per chain.

Amides #32 to #42 inclusive, crosslink when heated in the range of 235° C. to 375° C.

EXAMPLE IX

Preparation of Anhydride-Terminated Oligomeric Polyimide #3

Using the m-cresol-benzene azeotropic procedure, there is allowed to react BTCA (3.6251 g, 0.01125 mole) and DAPB3,3 (2.9223 g, 0.01 mole) in 40 ml of m-cresol and 10 ml of benzene. There is obtained 5.6071 g of polyimide #3 which is a light yellow powder soluble in m-cresol, DMAC, sulfolane and dioxane. On a Fisher-Johns melting point apparatus this melts at 120° C. with some evolution of gas. The TGA in air shows losses in air of 1% at 200° C.; 2% at 300° C.; 3% at 400° C.; 4% at 500° C. and 19% at 600° C. The elemental analysis shows 71.01% C, 3.22% H and 4.60% N, which values are in excellent agreement with the calculated values for the formula:

O(OC)₂C₆H₃COC₆H₃(CO)₂[NC₆H₄OC₆H₄OC₆H₄-N(OC)₂C₆H₃COC₆H₃(CO)₂]₈O

EXAMPLE X

Preparation of Anhydride-Terminated Polyimide #5

Using the procedure of Example III, BTCA (14.50 g, 0.045 mole) is reacted with SDA (9.9324 g, 0.04 mole) in 90 ml of cresol and 20 ml of benzene. Polyimide #5 is obtained (21.4 g) which is a light yellow solid soluble in m-cresol, DMAC, DMF and sulfolane. The lowest temperature at which a sample melts completely when dropped on a preheated block is 270° C. Its TGA in air shows losses of: 0% at 200° C.; 2% at 300° C.; 3% at 400° C.; 4% at 500° C. and 25% at 600° C. The elemental analysis shows 63.99% C, 2.73% H and 4.95% N, which values are in good agreement with the calculated values for the formula:

O(OC)₂C₆H₃COC₆H₃(CO)₂[NC₆H₄SO₂C₆H-4(OC)₂C₆H₃COC₆H₃(CO)₂]₈O

EXAMPLE XI

Preparation of Anhydride-Terminated Oligomeric Polyimide #6

Using the same azeotropic techniques as above, BTCA and 2,4-diaminotoluene (DAT) are reacted in a molar ratio of six to five to obtain polyimide #6 whose elemental analysis conforms with the formula:

O(OC)₂C₆H₃COC₆H₃(CO)₂[NC₆H₃(CH₃)-N(OC)₂C₆H₃COC₆H₃(CO)₂]₅O

EXAMPLE XII

Replacement of the BTCA in Example X by an equivalent amount of pyromellitic dianhydride produces polyimide #7 which has the formula:

O(OC)₂C₆H₂(CO)₂[NC₆H₃(CH₃)N(OC)₂C₆H₂-(CO)₂]₃O

EXAMPLE XIII

The anhydride-terminated polyimides #3, #4, #5, #6 and #7 are converted individually by the procedure of Example VIII to the diamide terminated polyimide corresponding to amides #35, 36, 38, 41 and 42. When heated alone or with dicumyl peroxide, each of these yields an insoluble, infusible, crosslinked polymer.

EXAMPLE XIV

By the procedure of Example VIII, benzophenonetetracarboxylic acid di-anhydride is converted to:

CH₂=CHCH₂\  
         N—OC          CO          CON / CH₂CH=CH₂  
CH₂=CHCH₂/                              \ CH₂CH=CH₂

CH₂=CHCH₂\                              / CH₂CH=CH₂  
         NOC                          CON  
CH₂CHCH₂/                              \ CH₂CH=CH₂

This, when heated to 300° C. becomes infusible and insoluble in 40-60 seconds.

Other monomeric aromatic tetracarboxylic acid dianhydrides such as listed above, may be substituted for the benzeophenonetetracarboxylic acid dianhydride to produce corresponding derivatives having 2-8 terminal crosslinking groups.

Typical of the various other products of this invention that may be produced by this procedure using monomeric dianhydrides are:

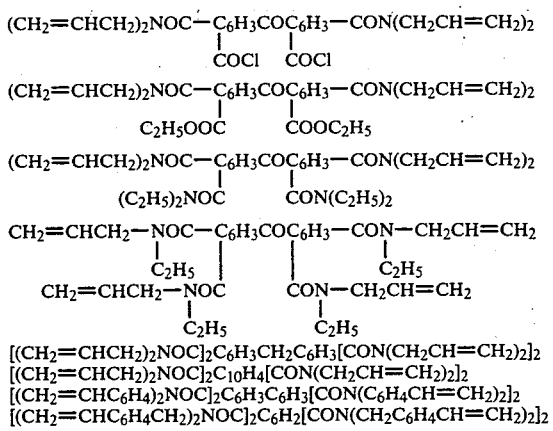

[(CH₂=CHCH₂)₂NOC]₂C₆H₃CH₂C₆H₃[CON(CH₂CH=CH₂)₂]₂
[(CH₂=CHCH₂)₂NOC]₂C₁₀H₄[CON(CH₂CH=CH₂)₂]₂
[(CH₂=CHC₆H₄)₂NOC]₂C₆H₃C₆H₃[CON(C₆H₄CH=CH₂)₂]₂
[(CH₂=CHC₆H₄CH₂)₂NOC]₂C₆H₂[CON(CH₂C₆H₄CH=CH₂)₂]₂

The above compounds may be mixed with unsaturated materials capable of polymerizing through its unsaturation and the crosslinking of such compositions is improved by the presence of such compounds to give harder and more durable products upon molding. Moreover these compounds may be molded by themselves by the use of various polymerization catalysts, i.e. peroxy and other free radical generating materials to give satisfactory molded products.

EXAMPLE XV

The procedure of Examples III, IVA and IVB are repeated five times except that an equivalent amount respectively is used of the following individual dianhydrides in place of the benzophenone-tetracarboxylic acid dianhydride used in Example III:
1. Pyromellitic dianhydride
2. 2,3,5,7-Naphthalene tetracarboxylic acid
3. 3,3′4,4′-Diphenyl tetracarboxyllic acid dianhydride
4. 2,2-Bis(3,4-dicarboxylphenyl)-propane dianhydride
5. Bis(3,4-dicarboxyphenyl)ether dianhydride.

The pyromellitic polyimide diaminde-diester product has the formula:

1.
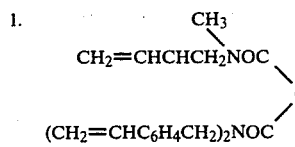
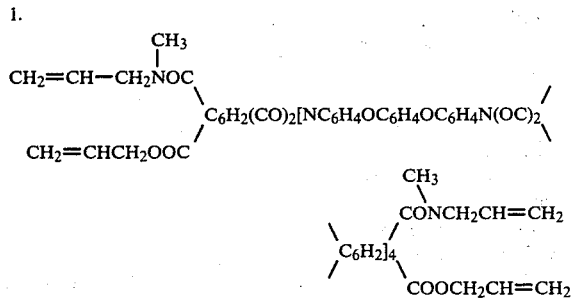

The other products have the same terminal groups as in the above formula but have the following intermediate structures respectively:

2.   >C₁₀H₄(CO)₂[NC₆H₄OC₆H₄OC₆H₄N(OC)₂C₁₀H₄]₄<
3.   >C₆H₃-C₆H₃(CO)₂[NC₆H₄OC₆H₄OC₆H₄N(OC)₂C₆H₃-C₆H₃]₄<
4.   >C₆H₃C₃H₆C₆H₃(CO)₂[NC₆H₄OC₆H₄OC₆H₄N(OC)₂C₆H₃C₃H₆C₆H₃]₄<
5.   >C₆H₃OC₆H₃(CO)₂[NC₆H₄OC₆H₄N(OC)₂C₆H₃OC₆H₃]₄<

EXAMPLE XVI

The procedures of Examples III, IVA, V and VII are repeated four times except that an equivalent amount respectively is used of the following individual diamines in place of the 1,3-di(3-aminophenoxy)benzene used in Example III and bis(4-vinylbenzyl)amine as the secondary amine used in Example VII:
1. 4,4′-Diaminodiphenyl
2. 4,4′-Diaminodiphenyl methane
3. 4,4′-Oxydianiline
4. 4,4′-Diaminobenzophenone The 4,4′-diaminodiphenyl polyimide tetramide product has the formula:

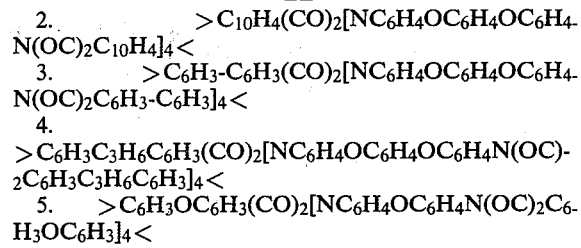

The other products have the same terminal groups as in the above formula but have the following intermediate structures respectively:
2.   C₆H₃COC₆H₃(CO)₂[NC₆H₄CH₂C₆H₄N(CO)₂C₆H₃COC₆H₃(CO)₂]₄
3.   C₆H₃COC₆H₃(CO)₂[NC₆H₄OC₆H₄N(CO)₂C₆H₃COC₆H₃(CO)₂]₄
4.   C₆H₃COC₆H₃(CO)₂[NC₆H₄COC₆H₄N(CO)₂C₆H₃COC₆H₃(CO)₂]₄

EXAMPLE XVII

A mixture of 30 parts of polyimide-amide #10, 70 parts of long fibered asbestos and 0.25 parts of cumyl peroxide is blended thoroughly and preformed into a one-inch disc which is compression molded at 1000 pounds per square inch at 265° C. for five minutes to yield a hard insoluble, infusible, molded product.

Similarly, a glass fiber reinforced composite is prepared by impregnating 181 E Glass Fabric with a solution of polyimide amide #10 in N-methyl pyrrolidinone to a total resin content of about 35% and the solvent removed by drying. The laminate is formed by stacking four sheets of impregnated glass fabric and curing at 250° C. at 200 pounds per square inch. The laminate is then post cured at 280° C. for 24 hours and the cured product shows a flexural strength value in excess of 45,000 psi.

Amide numbers 26, 27, 29, 35, 36, 38 and 42 also give similar satisfactory molded and laminated products.

Of particular utility in the practice of this invention are the hemi-amic acid derivatives of Formula I, in which Y″ represents OH or X. These can be converted to a large number of useful and valuable compositions. For example, as shown herein above, the hemi-amic acids can be converted to the hemi-amic acid halides which can and do react with active hydrogen containing compounds such as alcohols, amines and many other compounds containing active hydrogen. The formula of these hemi-amic acids can be written as:

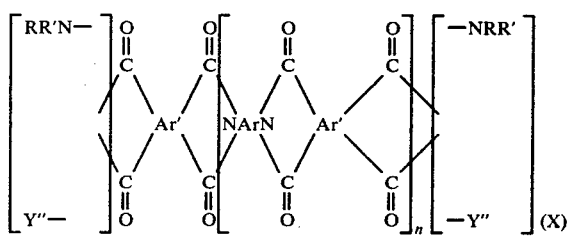

The various symbols have the same definitions as given for Formula I and Y" represents X or OH, with X representing halogen, of which chlorine is preferred.

While the vinyl group ($CH_2=CH-$) has been designated as the terminal unsaturated group, it is also contemplated as within the scope of the invention that substitution of small alkyl groups such as methyl, ethyl, etc. may be substituted for the alpha hydrogen in the vinyl group. Where such substitution does not interfere with polymerization, the alpha-alkyl derivatives are equivalent to vinyl and may be used instead, such as alpha-methyl vinyl, alpha-ethyl vinyl, etc.

While certain features of this invention have been described in detail with respect to various embodiments thereof, it will of course be apparent that other modifications can be made within the spirit and scope of this invention and it is not intended to limit the invention to the exact details insofar as they are defined in the following claims:

The invention claimed is:

1. A hemi-acid compound of the formula:

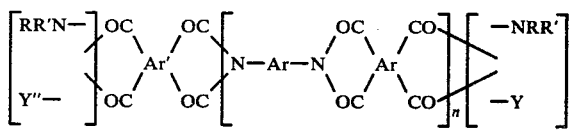

wherein:
Ar' is a tetravalent aromatic benzenoid radical, the four carbonyl groups being attached directly to separate carbon atoms and each pair of carbonyl groups being attached to adjacent carbon atoms in the Ar' radical except that in the case of the Ar' being a naphthalene radical one or both pairs of the carbonyl groups may be attached to peri carbon atoms;
Ar is a divalent aromatic benzenoid radical;
n is integer of at least one;
R' is an organic moiety containing 2 to 14 carbon atoms and having a terminal $-CH=CH_2$ structure; said organic moiety consisting of a hydrocarbon radical or two or three hydrocarbon radicals joined by $-O-$, $-SO_2-$ or $-COO-$ groups
R is an organic moiety containing one to 20 carbon atoms; said organic moiety consisting of a hydrocarbon radical or two or three hydrocarbon radicals joined by $-O-$, $-SO_2-$, or $-COO-$ groups
Y" is $-OH$ or X; and X is a halogen.
2. The hemi-amic acid compound of claim 1 in which Y" is OH.
3. The hemi-amic acid compound of claim 1 in which Y" is X.
4. The hemi-amic acid compound of claim 3 in which X is chlorine.
5. The hemi-amic acid compound of claim 4 in which R is R'.
6. The hemi-amic acid of claim 3 in which R' is $-CH_2CH=CH_2$.
7. The hemi-amic acid of claim 4 in which R' is $-CH_2CH=CH_2$.
8. The hemi-amic acid of claim 3 in which R is $-CH_3$.
9. The hemi-amic acid of claim 4 in which R is $-CH_3$.
10. The hemi-amic acid of claim 4 in which R is $-CH_2C_6H_4CH_2CH=CH_2$.
11. The hemi-amic acid compound of claim 4 in which R is $-CH_2C_6H_4CH=CH_2$.
12. The hemi-amic acid compound of claim 5 in which R and R' are $-CH_2CH=CH_2$.
13. The hemi-amic acid compound of claim 1 in which Ar' is a radical selected from the class consisting of:

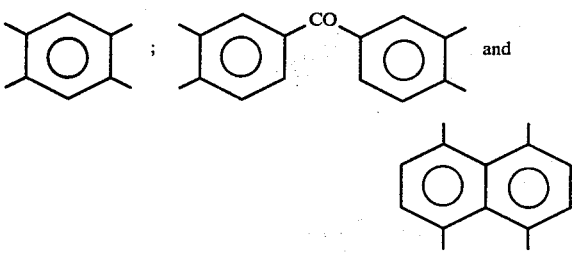

14. The hemi-amic acid compound of claim 1 in which Ar' is:

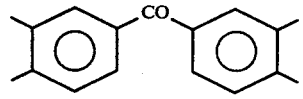

15. The hemi-amic acid compound of claim 1 in which n is at least one and the $>N-Ar-N<$ is the residue of a diamine is selected from the class consisting of:
1,3- and 1,4-$(NH_2)_2$benzene
2,3-; 2,5-; 2,6-and 3,5-$(NH_2)_2$toluene
3,3'-; 4,4' and 3,4'-methylene dianiline
4,4'-; 3,3'- and 3,4'-oxydianiline;
4,4'-; 3,3'- and 3,4'-sulfonyldianiline;
1,3-; 1,4- and 1,2-bis(3-aminophenoxy)benzyene; and
1,3- and 1,4-bis(4-aminophenoxy)benzene
16. The hemi-amic acid compound of claim 15 in which the diamine is a methylene dianiline.
17. The hemi-amic acid compound of claim 15 in which the diamine is a sulfonyl dianiline.
18. The hemi-amic acid compound of claim 15 in which the diamine is a oxydianiline.
19. The hemi-amic acid compound of claim 15 in which the diamine is 2,5-toluene diamine.

* * * * *

UNITED STATES PATENT AND TRADEMARK OFFICE
CERTIFICATE OF CORRECTION

PATENT NO. : 4,316,844
DATED : February 23, 1982
INVENTOR(S) : Phillip A. Waitkus and Gaetano F. D'Alelio It is certified that error appears in the above—identified patent and that said Letters Patent is hereby corrected as shown below:

Col. 1, line 61, change "or" to "on".

Col. 23, line 41, at the extreme right of the formula, change

Y to Y".

Col. 24, line 55, correct "benzyene" to read "benzene".

Signed and Sealed this

Eleventh Day of May 1982

[SEAL]

Attest:

Attesting Officer

GERALD J. MOSSINGHOFF
Commissioner of Patents and Trademarks